United States Patent [19]

Kelman

[11] Patent Number: 4,534,069
[45] Date of Patent: Aug. 13, 1985

[54] INTRAOCULAR LENS AND METHOD OF POSITIONING THE SAME IN AN EYE

[76] Inventor: Charles D. Kelman, North Shore Towers—269 Grand Central Pkwy., Floral Park, N.Y. 11005

[21] Appl. No.: 574,676

[22] Filed: Jan. 27, 1984

[51] Int. Cl.[3] .......................... A61F 1/16; A61F 1/24
[52] U.S. Cl. ............................................. 623/6; 427/2
[58] Field of Search .............................. 3/13, 1; 427/2

[56] References Cited

U.S. PATENT DOCUMENTS

| | | | |
|---|---|---|---|
| 4,159,546 | 7/1979 | Shearing | 3/13 |
| 4,240,163 | 12/1980 | Galin | 3/13 |
| 4,249,271 | 2/1981 | Poler | 3/13 |
| 4,251,887 | 2/1981 | Anis | 3/13 |
| 4,363,143 | 12/1982 | Callahan | 3/13 |
| 4,463,457 | 8/1984 | Kelman | 3/13 |

OTHER PUBLICATIONS

Lens Implantation (Book) by P. Leonard et al., Dr. W. Junk Publishers, Printed in Belgium 1982, pp. 448–449.

Primary Examiner—Ronald L. Frinks
Attorney, Agent, or Firm—Henry Sternberg

[57] ABSTRACT

An intraocular lens and method of positioning the same in an eye in which the lens includes a layer of material which is soluble in the eye for maintaining the position-fixation members of the lens in contracted condition during insertion thereof into the eye.

11 Claims, 7 Drawing Figures

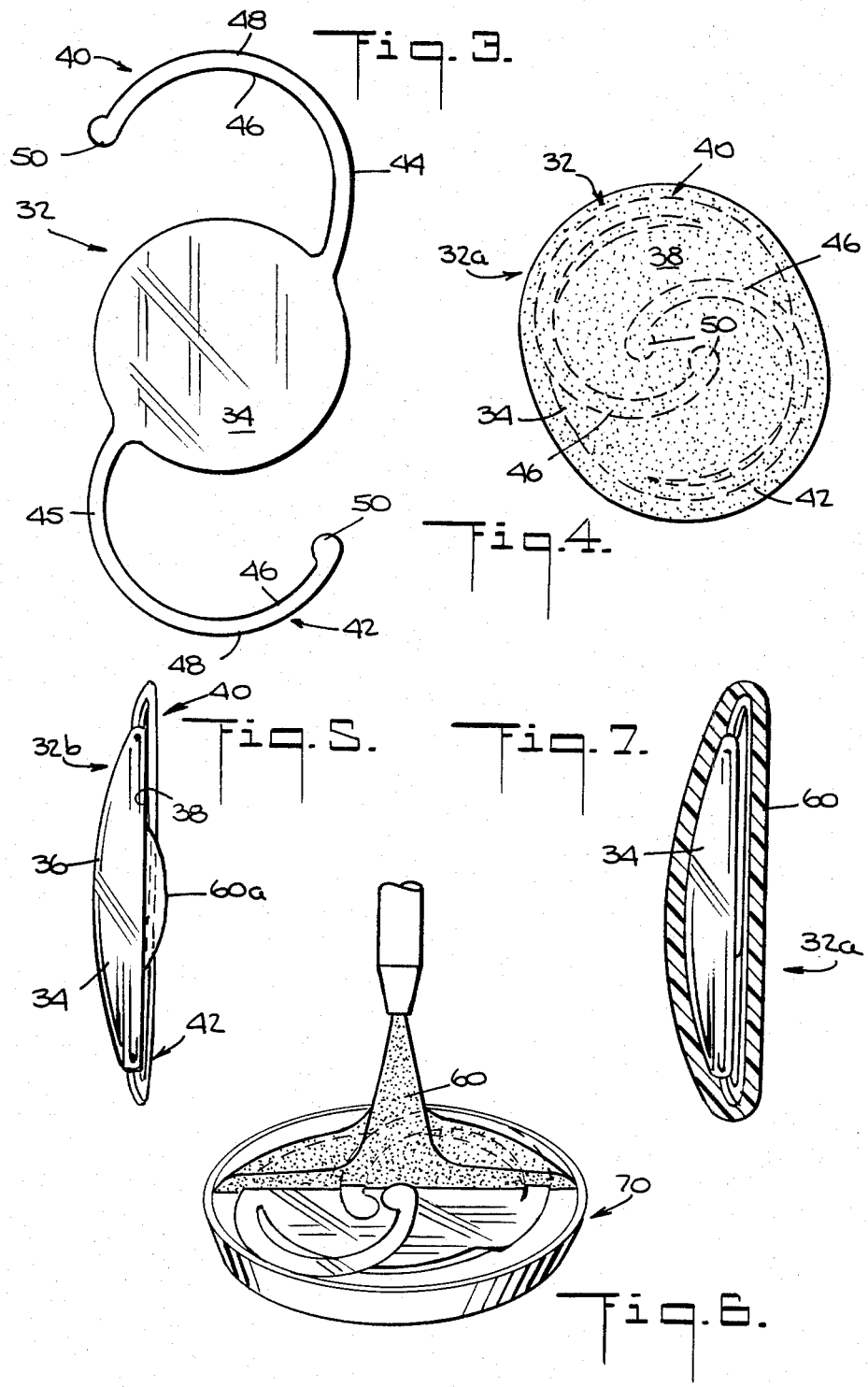

INTRAOCULAR LENS AND METHOD OF POSITIONING THE SAME IN AN EYE

This invention relates to intraocular lenses for the human eye and, more particularly, to intraocular lenses of the type which can be positioned in the posterior chamber of the eye. The invention also relates to methods of positioning such lenses in an eye.

One type of posterior chamber intraocular lens is described and claimed in U.S. Pat. No. 4,159,546 issued July 3, 1979 to S. P. Shearing. Such a lens includes a lens body and position-fixation means extending therefrom. The lens is inserted into the eye through a corneoscleral incision. To minimize the possibility of injury to the eye, the position-fixation means may comprise a pair of flexible members, or haptics, which easily bend and preferably have a memory. While the flexibility and resilience of the position-fixation members is necessary after insertion so that they exert sufficient pressure to maintain the lens seated in the eye yet do not exert enough pressure to cause injury, to the eye, nevertheless, such springy position-fixation members extending from the lens body are a complication to the surgeon trying to insert the lens into the posterior chamber of the eye.

It is an object of the present invention, therefore, to provide a new and improved intraocular lens which avoids one or more of the limitations of prior such lenses.

It is another object of the invention to provide a new and improved intraocular lens whose haptics are captive during insertion into the eye and are allowed to expand after insertion into the eye.

It is another object of the invention to provide a new and improved method of positioning an intraocular lens in an eye which avoids one or more of the limitations of prior such methods.

In accordance with the invention, an intraocular lens comprises a lens body and position-fixation means extending from the lens body and having a portion remote from the lens body for positioning the lens body within an eye. The position-fixation means is deformable between an expanded condition in which said portion is remote from the lens body and a contracted condition in which said portion is adjacent to the lens body. The lens also includes a material, which is soluble in the eye, connecting the lens body to the remote portion of the position-fixation means when the latter is in the contracted condition thereof for holding the position-fixation means captive during insertion thereof into the eye.

Also in accordance with the invention, a method of positioning an intraocular lens in an eye, the lens comprising a lens body and position-fixation means extending from the lens body and having a portion remote from the lens body for positioning the lens body within the eye, comprises applying to the lens a material which is soluble in the eye for connecting the lens body to the remote portion of the position-fixation means when the latter is in contracted condition thereof for holding the position-fixation means captive in such contracted condition thereof during insertion of the lens into an eye. The method also includes inserting the lens into the eye through an opening in the eye and seating the lens in the eye.

For a better understanding of the present invention together with other and further objects thereof, reference is made to the following description, taken together with the accompanying drawings, and its scope will be pointed out in the appended claims.

Referring now to the drawings:

FIG. 3 is a plan view of the intraocular lens represented in FIG. 1 showing the position-fixation means in expanded condition thereof;

FIG. 4 is a plan view of another embodiment of the intraocular lens according to FIG. 2 just prior to insertion into the eye;

FIG. 5 is a side elevational view of another embodiment of the intraocular lens according to the present invention;

FIG. 6 is a diagrammatic perspective view of a mold for an intraocular lens in accordance with the invention; and FIG. 7 is a transverse sectional view of the intraocular lens of FIG. 4.

Figure 1:
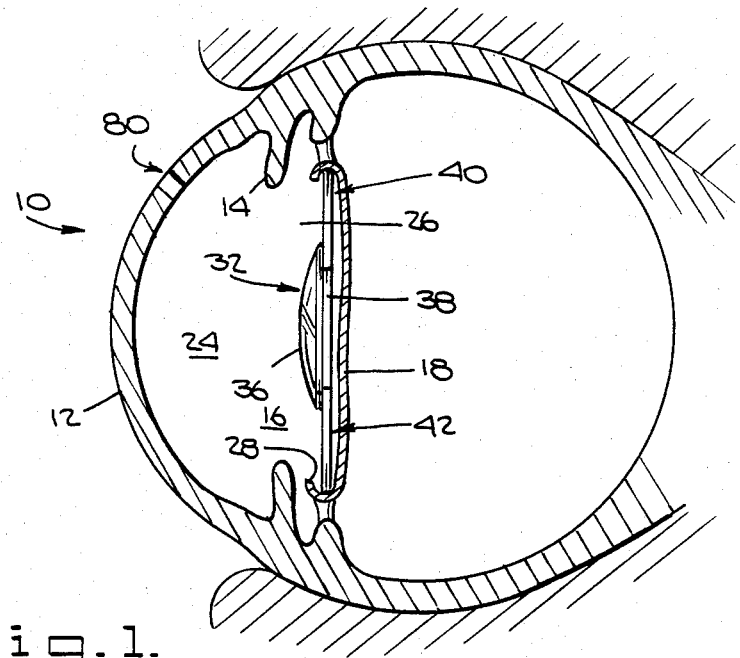
FIG. 1 is a simplified schematic sectional view of an eyeball implanted with an intraocular lens according to the present invention.
Figure 2:
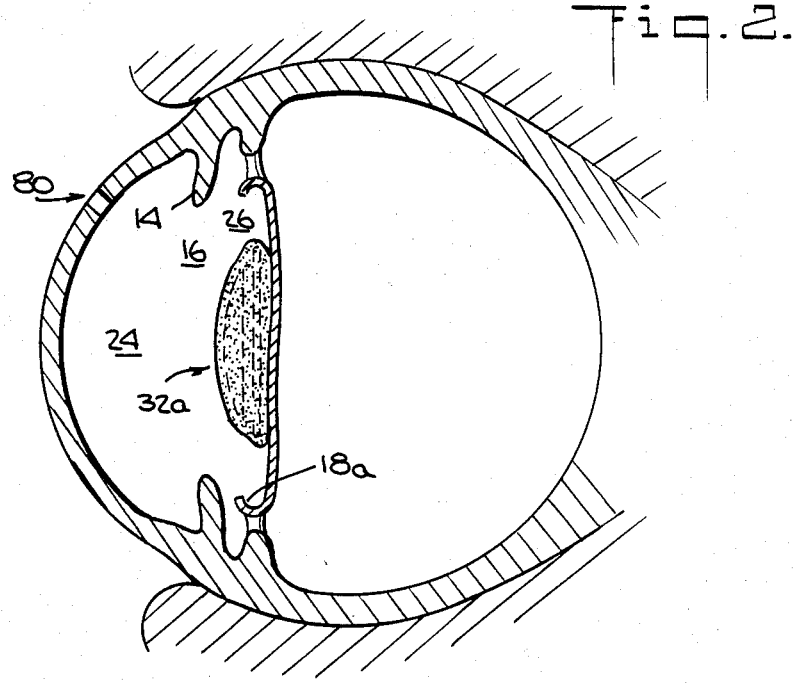
FIG. 2 is a simplified schematic sectional view of an eyeball showing the intraocular lens embodying the preferred form of the present invention just prior to seating thereof in the posterior chamber.

Referring now more particularly to FIGS. 1 and 2 of the drawings, reference numeral 10 generally designates an eyeball as shown in simplified schematic cross-section in FIG. 1. Portions of the eyeball structure which are not believed to be essential to an understanding of the invention have been omitted for the sake of clarity.

The eyeball 10 includes a cornea 12, an iris 14 having a central opening or pupil 16, a posterior capsule 18 and the remainder of an anterior capsule 28 after extracapsulary removal of a cataracted natural lens. The posterior capsule defines at its upper and lower interior peripheral regions, respectively, a cul-de-sac 18a formed between the posterior and the anterior capsules. An aqueous zone, between the cornea 12 and the membrane 18, is divided by the iris 14 into an anterior chamber 24 and a posterior chamber 26.

An intraocular artificial lens for the eyeball 10 is generally indicated by reference numeral 32 in FIG. 1 and will be described generally with reference to FIGS. 3 and 4. The lens 32 can be formed of any suitable material which is compatible with the environment of the eyeball, such as a non-toxic plastic, for example, polymethylmethacrylate and may have one or both of its position fixation members of an even more flexible material as, for example, polypropylene.

The lens 32 includes a light-focusing lens body 34, or optic, having, for example, a convex anterior surface 36 and a generally flat posterior surface 38. Extending from the lens body 34 are position-fixation means which comprise, for example, a pair of oppositely disposed symmetrical position-fixation members 40 and 42 which include respective connecting stem portions 44 and 45 that extend from the periphery of the lens body 34.

Referring to FIG. 3, the connecting stem portions 44 and 45 individually have identical limb portions 46, 46 joined thereto and extending transversely thereof and remote from the lens body 34. A convex outer seating edge 48 of each of the limb portions 46, 46 terminates with respective lobes 50, 50. The lens body 34 may, for example, have a diameter of 5 mm and a thickness of 0.4 mm. For example, the thickness of each of the position-fixation members 40 and 42 may be 0.2 mm and the width thereof, in the plane of the paper, about 1.2 mm. The distance between corresponding points on the outer edge portions 48, 48 from one of the members 40, 42 to the other may be, for example, about 13 mm, when the lens is in the initial undeformed condition thereof shown in FIG. 3.

The limb portions 46, 46 of the position-fixation members 40, 42 are adapted to seat in the cul-de-sac 18a formed between the anterior and posterior capsules, as shown in FIG. 1.

Referring now more particularly to the preferred embodiment shown in FIGS. 2, 4 and 7 of the drawings, the position-fixation means of the lens 32 are shown in contracted, captive, conditon. Just prior to insertion of the lens into the eye, the position fixation members 40, 42 are temporarily deformed to assume a position in which the respective lobes 50, 50 are preferably each overlying a central portion of the posterior surface 38 of the lens body 34. The position-fixation members are temporarily maintained captive in this deformed condition by a coating of a material 60, which is soluble in the eye. The coating material 60 covers the lens body 34 and the position-fixation means, including the remote portions of the position-fixation means, i.e. the limbs 46, 46 of the position-fixation members 40, 42, thereby fully encapsulating the lens 32, in its contracted condition, for facilitating insertion thereof into the eye, first through the incision 80 and then through the pupil 16. The encapsulated lens is designated by reference numeral 32a on FIG. 7.

The coating material 60 is preferably chondroitin sulfate or sodium hyaluronate, or a mixture of both sufficiently concentrated to form a dryable viscous coating around the lens. Alternatively, material 60 may be a material having at least a component of human blood such as fibrin or may, for example, be coagulated whole human blood. In finished form, the coating 60 forms a dry layer, preferably about 0.25 mm thick around the lens. The layer of material 60 may also be, for example, a layer of gelatin which is dried by exposure to the air, or starch paste made from a mixture of flour and water. The layer of material 60 may also be any other material which is (a) non-toxic and otherwise compatible with the fluid in the human eye, (b) soluble in the fluid in the eye, (c) dryable or otherwise changeable from a liquid state into a semi-rigid or rigid state and capable of adhering to and/or encapsulating the lens for maintaining the position-fixation members in deformed, captive condition with the remote portions thereof in adhering relation with the optic, or lens body, so as to reduce the size of the lens overall and to add rigidity to the entire structure.

The coating of material 60 may be applied to the lens 32, after the position fixation members have been placed into their deformed condition, by coating the lens with wet material of the type described above, as by brushing or by dipping the lens 32 in such wet material thereby encapsulating the lens 32, or by pouring the wet material 60 into a mold 70, as seen in FIG. 6, and positioning the lens in such mold either before or after the material 60 has been poured, or by any other suitable technique. The layer of material 60 may then dry on the lens 32 forming a coating around both the optic and the position fixation members for maintaining the latter in contracted condition. The coated lens 32a may then be inserted into the eye through the opening 80 and through the pupil 16 into the posterior chamber 26. It will be seen that the layer 60 forms the lens 32a into a unitary body facilitating the insertion of the lens into the eye. After the lens is inside the eye the layer of material 60 begins to dissolve naturally in the fluid of the eye and the surgeon may, by merely holding the lens in proper position in the posterior chamber, e.g. the position represented in FIG. 2, seat the position-fixation members 40, 42. As the material 60 dissolves, the position fixation members will expand toward their undeformed i.e. expanded condition shown in FIG. 3, thus seating themselves in the posterior capsule cul-de-sac 18a.

Seating known intraocular lenses in the posterior chamber is at best a difficult procedure. The difficulties are compounded by (a) the difficulty or impossibility for the surgeon to see the seating locations in the dark recesses behind the iris (b) the difficult manipulation required to insert, through the pupil, a lens with remote position-fixation means extending from a central optic without causing injury to the iris and (c) the need to depress the upper position-fixation member 40 toward the first-seated position-fixation member 42 in order to insert the upper fixation member through the pupil thus risking injury to the tissue in which the first member is seated. These risks are substantially minimized with the lenses according to the present invention since the lens is in contracted condition when inserted through the pupil and may be readily held in proper centralized position by the surgeon while the material 60 dissolves to permit the position-fixation means to expand into seating condition without any additional pressure exerted against the tissues at the interior of the eye as a consequence of the seating procedure.

It will be understood that the invention has applications with many other configurations of lenses. The coating material, after it has dried, serves to encapsulate the lens, as described above, holding the position-fixation means captive in contracted condition during insertion of the lens into and implantation of the lens in the eye, but will be dissolved after a short time, i.e. preferably less than two minutes, by the fluid in the eye, so that the position-fixation members will then again spring loose and exhibit the desired flexibility.

Referring now to FIG. 5 of the drawings, it will be understood that in lieu of fully encapsulating the lens, a drop or dab 60a of the material 60 may be placed over the region on the posterior surface 38 at which the free end portions 50,50 of the position fixation means are located when the latter is in deformed i.e. contracted condition, for encapsulating such free end portions and adhering them to the lens body. After the drop of material 60a has dried, the procedure to insert the lens 32a may begin.

It should be noted that polypropylene and other similarly springy materials, commonly used for the position-fixation members of intraocular lenses, take on a permanent set in a relatively short span of time, i.e. in a matter of hours, if kept in substantially deformed condition such as the condition shown in FIG. 4. Therefore, the encapsulation described herein must preferably be accomplished just prior to the implant surgery.

While there have been described what are at present considered to be the preferred embodiments of this invention, it will be obvious to those skilled in the art that various changes and modifications may be made therein without departing from the invention, and it is, therefore, aimed to cover all such changes and modifications as fall within the true spirit and scope of the invention.

What is claimed is:
1. An intraocular lens comprising:
   a lens body;

resilient position-fixation means for positioning said lens body within an eye, said position-fixation means having a first portion integrally connected with and extending from said lens body and having a second portion extending from said first portion, and said position fixation means being deformable between an expanded condition in which said second portion is remote from said lens body and a contracted condition in which said second portion is adjacent to said lens body; and a layer of material which is soluble in the eye, connecting said lens body to said second portion of said position-fixation means in said contracted condition thereof, thereby maintaining said position-fixation means in said contracted condition during insertion thereof into the eye.

2. An intraocular lens in accordance with claim 1 in which said first portion of said position-fixation means is a stem portion, said second portion of said position-fixation means is a limb portion, and said lens includes a pair of said stem portions and a pair of said limb portions and each said limb portion is in substantially overlying relation with said lens body.

3. An intraocular lens in accordance with claim 2 in which said layer substantially encapsulated both said lens body and said position-fixation means in said contracted condition thereof.

4. An intraocular lens in accordance with claim 1 in which said material is chosen from the group consisting of human blood, fibrin, and gelatin.

5. An intraocular lens in accordance with claim 1 in which said material is (a) non-toxic and otherwise compatible with the fluid in the human eye, (b) soluble in the fluid in the eye (c) dryable from a liquid state into a semi-rigid or rigid state and capable of adhereing to and/or encapsulating the lens.

6. An intraocular lens in accordance with claim 1 in which said material is chosen from the group consisting of chondroitin sulfate, sodium hyaluronate, or a mixture of chondroitin sulfate and sodium hyaluronate.

7. A method of positioning an intraocular lens in an eye, the lens comprising a lens body and resilient position-fixation means for positioning said lens body within an eye, said position-fixation means having a first portion extending from said lens body and having a second portion extending from said first portion, and said position-fixation means being deformable between an expanded condition in which said second portion is remote from said lens body and a contracted condition in which said second portion is adjacent to said lens body, comprising:

deforming said position-fixation means into said contracted condition thereof;

applying to said lens with deformed position-fixation means a layer of material which is soluble in the eye;

connecting said lens body to said adjacent second portion of said position-fixation means with said material to maintain said position-fixation means in said contracted condition thereof;

inserting said lens into the posterior chamber of the eye; and allowing said material to dissolve in the eye for seating said lens in the eye.

8. A method in accordance with claim 7 in which the step of applying to said lens a layer of material comprises applying to said lens a layer of wet material and which includes the step of drying said material while holding said position-fixation means in said contracted condition thereof just prior to insertion thereof into the eye.

9. A method in accordance with claim 7 in which the step of applying to said lens a layer of material comprises applying to said lens a layer of wet material and which includes the step of permitting said material to harden just prior to insertion thereof into the eye.

10. A method in accordance with claim 7 in which the step of applying said layer of material comprises placing said lens into a mold adapted to hold the position-fixation means in said contracted condition thereof and pouring said material into said mold.

11. A method in accordance with claim 7 wherein said step of applying said layer of material comprises encapsulating substantially all of said lens body and said position-fixation means with said material.

* * * * *